(12) United States Patent
Schwarz et al.

(10) Patent No.: US 6,583,326 B2
(45) Date of Patent: Jun. 24, 2003

(54) PROCESS FOR SEPARATING PHENOL FROM A MIXTURE COMPRISING AT LEAST HYDROXYACETONE, CUMENE, WATER AND PHENOL

(75) Inventors: Christoph Schwarz, Marl (DE); Markus Weber, Haltern (DE); Uwe Tanger, Bochum (DE); Hermann-Josef Korte, Haltern (DE); Jochen Ullrich, Gladbeck (DE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/970,856

(22) Filed: Oct. 5, 2001

(65) Prior Publication Data

US 2002/0066661 A1 Jun. 6, 2002

(30) Foreign Application Priority Data

Dec. 6, 2000 (DE) .......................... 100 60 505

(51) Int. Cl.⁷ .............................................. C07C 37/68
(52) U.S. Cl. ........................... 568/754; 203/28; 203/39; 568/798
(58) Field of Search ................................. 568/754, 798; 203/28, 39

(56) References Cited

U.S. PATENT DOCUMENTS

| 3,029,294 A | * | 4/1962 | Keeble |
| 3,322,651 A | | 5/1967 | Nielsen et al. |
| 3,405,038 A | * | 10/1968 | Kohmoto |
| 4,251,325 A | * | 2/1981 | Marsh |
| 4,298,765 A | * | 11/1981 | Cochran |
| 4,328,377 A | * | 5/1982 | Mori |
| 4,333,801 A | * | 6/1982 | Pujado |
| 4,340,447 A | * | 7/1982 | Laverick |
| 4,832,796 A | * | 5/1989 | Fulmer |
| 5,064,507 A | | 11/1991 | O'Donnell et al. |
| 5,264,636 A | * | 11/1993 | Shirahata |
| 5,456,806 A | * | 10/1995 | Lorenzoni |
| 6,066,767 A | * | 5/2000 | Zakoshnasky |

FOREIGN PATENT DOCUMENTS

| EP | 190790 A1 | * | 8/1986 |
| GB | 1 021 759 | | 3/1966 |

* cited by examiner

Primary Examiner—Michael L. Shippen
(74) Attorney, Agent, or Firm—Oblon, Spivak, McClelland, Maier & Neustadt, P.C.

(57) ABSTRACT

Phenol is separated from a mixture containing hydroxyacetone, cumene, water and phenol, by fractionating the mixture in a process with a fractional distillation step and a phase separation step to provide a single phenol fraction containing less than 300 ppm of hydroxyacetone. In the work-up by distillation of cleavage product mixtures, the hydroxyacetone can be removed from the cleavage product mixture together with a phenol fraction from which the hydroxyacetone has to be removed. A process can be used for purifying cleavage product mixtures obtained in the cleavage of alkylaryl hydroperoxides such as cumene hydroperoxide. The process allows separation of phenol and acetone from mixtures obtained in the cleavage of cumene hydroperoxide.

13 Claims, 2 Drawing Sheets

PROCESS FOR SEPARATING PHENOL FROM A MIXTURE COMPRISING AT LEAST HYDROXYACETONE, CUMENE, WATER AND PHENOL

BACKGROUND OF THE INVENTION

1. Field of the Invention

The invention relates to an improved process for separating phenol from a mixture containing hydroxyacetone, cumene, water and phenol. The invention also includes an apparatus for separating phenol from cleavage product mixtures and a composition containing cumene and α-methylstyrene.

DISCUSSION OF THE BACKGROUND

The process for the acid-catalyzed cleavage of cumene hydroperoxide into phenol and acetone has been of particular industrial importance for a long time. In the preparation of phenol from cumene by the Hock process, cumene is oxidized to cumene hydroperoxide (CHP) in a first reaction step, known as oxidation, and the CHP is subsequently concentrated to from 65 to 90% by weight in a vacuum distillation step, known as concentration. In a second reaction step, known as cleavage, the CHP is cleaved into phenol and acetone by action of an acid, usually sulfuric acid. In addition to phenol and acetone, the cleavage product further comprises additional compounds which may be formed in the reaction steps preceding the cleavage and which are only partly transformed, if at all, in the cleavage. The most important compounds present in the cleavage product in addition to phenol and acetone are, in particular, α-methylstyrene (AMS), cumene and acetophenone. In addition, small amounts of dimethyl phenyl carbinol (DMPC) formed in the oxidation can be present in the cleavage product. Further impurities include compounds such as methylbenzofuran (MBF), hydroxyacetone, mesityl oxide (MO) and carbonyl compounds such as acetaldehyde and 2-phenylpropionaldehyde. After neutralization of the cleavage product and optional removal of an aqueous phase, the cleavage product is worked up by distillation.

2. Description of the Related Art

Various processes for working up the cleavage product by distillation are known (Ullmann's Encyclopedia of Industrial Chemistry, 5th completely revised edition, Vol. A19, 1991, VCH Verlagsgesellschaft mbH, Weinheim; incorporated herein by reference). These processes involve initial neutralization of the cleavage product using aqueous sodium hydroxide, amines or aqueous phenoxide solution. After phase separation, the organic part of the neutralized cleavage product is transferred to a first column in which crude acetone is distilled off from the remaining cleavage product via the top of the column. This crude acetone is usually treated with alkali in a scrubber and once again purified by distillation. However, the scrub is sometimes also carried out in the column. The bottom product from the first column is distilled in a second column from which AMS and cumene are taken off at the top and are usually passed to a hydrogenation step in which cumene is generated. AMS and cumene can also be separated off by azeotropic distillation in the presence of water. The bottom product remaining in the second column is distilled in a crude phenol column.

The crude phenol obtained by this process can be purified further by extractive distillation using water or by treatment with an acid ion exchanger and subsequent distillation. In the latter process, compounds which are difficult to separate from phenol by distillation, e.g. mesityl oxide and hydroxyacetone, are condensed to form higher-boiling compounds.

Such a process is described, for example, in U.S. Pat. No. 5,064,507, incorporated herein by reference. In this process, the cleavage product is first separated from the crude acetone in a crude acetone column. The bottom product is transferred to a cumene column in which cumene and AMS are separated from the cleavage product. The column is, however, operated so that a certain proportion of AMS remains in the bottom product since it is required as a reactant or solvent in the further processing of the phenol to remove MBF and other impurities. This bottom product is reacted with an amine, preferably hexamethylenediamine, in a reactor having plug flow characteristics in order to convert carbonyl compounds, e.g. acetol (hydroxyacetone) or MO, into higher-boiling compounds. The product which has been treated in this way is worked up further by distillation. However, it passes through a further four columns and two reaction zones before the purified end product phenol is obtained. The outlay for apparatus required for the removal of the hydroxyacetone from the phenol is relatively high in this process.

U.S. Pat. No. 3,322,651, incorporated herein by reference, also describes the use of nitrogen compounds, in particular amines, for purifying phenol obtained in the cleavage of CHP. However, the amines have to be removed again from the products.

GB 1 021 759, incorporated herein by reference, describes the work-up of a cleavage product mixture obtained from the acid-catalyzed cleavage of CHP and from which the catalyst has been removed by neutralization and scrubbing. To be able to obtain a phenol having a low hydroxyacetone content, the separation is carried out by feeding the cleavage product mixture into a distillation column at a side inlet and fractionating this mixture in one separation step to give a top fraction comprising water, acetone, hydroxyacetone and cumene and a bottom fraction comprising phenol having a hydroxyacetone content of less than 100 ppm. Depending on the composition of the cleavage product mixture, cumene was added in an amount so that the ratio of cumene to phenol in the feed to the column was at least 0.28 part by weight of cumene to 1 part by weight of phenol, since the process is based on the separation of an azeotropic mixture of hydroxyacetone and cumene from the phenol. The hydroxyacetone can be removed from the phenol by this process. However, a top fraction which comprises not only water, cumene and hydroxyacetone but also acetone is obtained. Phenol contamination may also be present in the top fraction. These products likewise have to be separated from one another.

In U.S. Pat. No. 4,251,325, incorporated herein by reference, the work-up of a fraction which has been substantially freed of low boilers, water and acetone has been optimized by operating the cumene column in such a way that a mixture comprising cumene, AMS and hydroxyacetone is taken off at the top, with this mixture being separated virtually completely from the crude phenol remaining in the bottoms and thus not having to be removed in a costly fashion during the work-up of the phenol. This process gives phenol containing less than 30 ppm of hydroxyacetone. A disadvantage of this process is the fact that the input mixture has to be substantially free of water, which is why an acetone fraction comprising low boilers and also the major part of the water present in the cleavage product mixture has to be separated from the cleavage product mixture in the preceding separation step. The work-up of such an acetone fraction by methods of the prior art is relatively uneconomical, since a high outlay in terms of apparatus is required.

BRIEF DESCRIPTION OF THE FIGURES

A more complete appreciation of the invention and many of the attendant advantages thereof will be readily obtained as the same becomes better understood by reference to the following description and FIGS. 1 and 2, which Figures show embodiments of the invention with phase separation after and before the distillation column, respectively.

SUMMARY OF THE INVENTION

Figure 1:
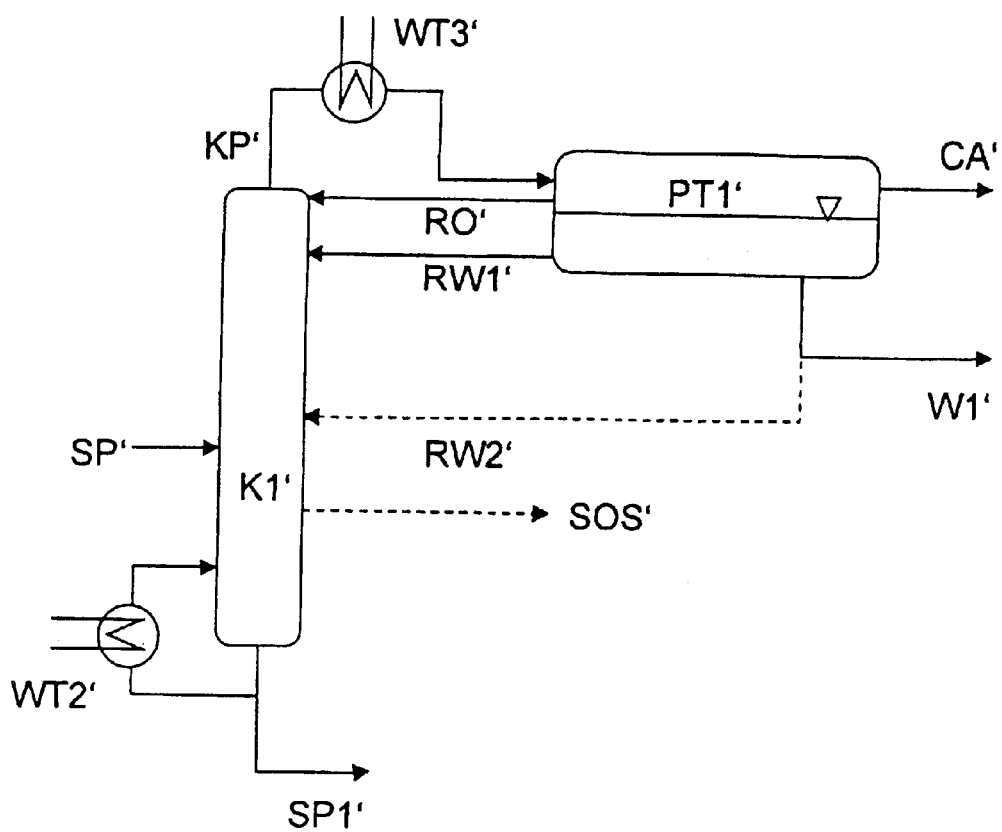

It is therefore an object of the present invention to provide a simple process for separating phenol from a mixture comprising at least cumene, phenol and hydroxyacetone, in which process a phenol having a hydroxyacetone content of less than 30 ppm is separated from the mixture with a low energy consumption, with a low outlay in terms of apparatus, and in the presence of water.

It has surprisingly been found that a mixture comprising at least phenol, water, hydroxyacetone and cumene can be worked up by means of a single fractional distillation step with subsequent phase separation to give phenol having a hydroxyacetone content of less than 30 ppm, with this fractional distillation step being able to be carried out with a lower energy consumption and a lower outlay in terms of apparatus than in conventional processes. Likewise surprisingly, it has been found that reversal of the order of the process steps also enables phenol having a hydroxyacetone content of less than 30 ppm to be separated from the abovementioned mixture. As used herein "less than 30 ppm" means all values under 30 ppm such as 25, 20, 15, 10, 5, 3, 2 and 1 ppm.

The present invention accordingly provides a process for separating phenol from a mixture comprising at least hydroxyacetone, cumene, water and phenol, which comprises fractionating the mixture by means of at least one fractional distillation step and at least one phase separation step in such a way that at least one phenol-containing fraction containing less than 300 ppm of hydroxyacetone is obtained. As used herein "less than 300 ppm" means all values under 300 ppm such as 250, 200, 150, 100, 50, 25, 10, 5, 2 and 1 ppm.

The present invention likewise provides an apparatus for separating phenol from a mixture comprising at least hydroxyacetone, cumene, water and phenol, which comprises at least one distillation column which is dimensioned so that at least a cumene- and/or α-methylstyrene-containing fraction can be taken off at the top of the column and a phenol-containing fraction having a hydroxyacetone content of less than 300 ppm can be taken off at the bottom of the column and at least one phase separation apparatus for separating organic phases from aqueous phases.

The invention also provides phenol obtained by means of a process for separating phenol from a mixture comprising at least hydroxyacetone, cumene, water and phenol, which comprises fractionating the mixture by means of at least one fractional distillation step and at least one phase separation step in such a way that at least one phenol-containing fraction containing less than 300 ppm of hydroxyacetone is obtained.

The invention also provides a mixture of cumene and AMS obtained by means of a process for separating phenol from a mixture comprising at least hydroxyacetone, cumene, water and phenol, which comprises fractionating the mixture by means of at least one fractional distillation step and at least one phase separation step in such a way that at least one phenol-containing fraction containing less than 300 ppm of hydroxyacetone is obtained.

The advantage of the process of the invention is that the separation step used in the distillation substantially simplifies the further work-up of both the cleavage product mixture and any individual fractions obtained from the cleavage product mixture. In particular, the joint removal of hydroxyacetone, AMS and cumene from the phenol-containing remainder of the cleavage product mixture substantially simplifies the work-up of the phenol-containing fraction. The steps carried out in conventional processes, in which the hydroxyacetone remains in the phenol-rich fraction and is removed therefrom by reacting the hydroxyacetone with phenol to form compounds which have a boiling point higher than that of phenol and can be separated from the phenol by distillation, become unnecessary.

Compared to conventional processes, the process of the invention has a significantly more favorable energy balance and also gives a higher total yield of phenol based on the phenol content of the cleavage product mixture. In contrast, the conventional procedure requires a relatively high energy input. In addition, the yield of phenol is reduced in conventional processes since the hydroxyacetone reacts with the phenol. The addition of expensive chemicals such as amines adds further cost. The removal of these chemicals and their by-products is also costly. The process of the invention, which circumvents this problem by separating the hydroxyacetone together with the cumene from the cleavage product mixture, requires a significantly lower outlay in terms of apparatus. Both the number of distillation columns required and also the number of reaction apparatuses necessary for reducing the contents of the various by-products in the fractions are reduced.

A further advantage achieved by the process of the invention is that the hydroxyacetone is preferentially obtained in an aqueous phase and can easily be disposed of or worked up together with this.

DETAILED DESCRIPTION OF THE INVENTION

For the purposes of the present invention, the total number of trays present in a column is defined as having a separation potential of 100% regardless of the number of trays, so that it is possible to indicate the region having a similar separation potential in columns having a differing number of trays. Accordingly, the bottom of the column, i.e. the region below the first tray, has a separation potential of 0%. At the top of the column, i.e. the region above the uppermost tray, the separation potential is, in accordance with this definition, 100%. In accordance with this definition, a column having 50 trays has a separation potential of about 30% in the region of the 15th tray.

The process of the invention can be used for the work-up by distillation of mixtures obtained as part of the cleavage product mixtures in the cleavage of cumene hydroperoxide (CHP) into acetone and phenol with subsequent work-up of the cleavage product mixture. The process of the invention is preferably used for separating phenols from a mixture which comprises at least hydroxyacetone, cumene, water and phenol and is preferably that part of a cleavage product mixture which is obtained after separation of crude acetone from the cleavage product mixture. The acetone content of such a mixture is preferably less than 1% by weight, very particularly preferably less than 0.2% by weight.

The process of the invention is described below by way of example for the work-up by distillation of a mixture obtained in the acid-catalyzed homogeneous cleavage of CHP and subsequent work-up of the cleavage product mixture. The process of the invention is not limited to the embodiments to the embodiment specifically described herein. This mixture is obtained as part of the cleavage product mixture by separating a crude acetone fraction from the cleavage product mixture.

The process of the invention for separating phenol from a mixture comprising at least hydroxyacetone, cumene, water and phenol, comprises fractionating the mixture by means of at least one fractional distillation step and at least one phase separation step in such a way that at least one phenol-containing fraction containing less than 300 ppm of hydroxyacetone is obtained. This phenol-containing fraction is very particularly preferably obtained by a process in which a single fractional distillation step and a single phase separation step are carried out.

Before the phenol is separated off, the mixture preferably has a phenol concentration of from 20 to 99% by weight, particularly preferably from 40 to 70% by weight, including all values and subranges therebetween such as 30,35, 45, 55, 65, 75, 48–64% by weight, etc. The mixture can have a hydroxyacetone concentration of from 300 ppm to 5% by weight.

Apart from the compounds mentioned, the mixture may further comprise additional compounds. Examples include α-methylstyrene (AMS), cumene, water, phenylbutenes, methylbenzofuran (MBF), dimethyl phenyl carbinol (DMPC), cresols, e.g. o-cresol, mesityl oxide (MO), n-propylbenzene, isopropylphenol, carbonyl compounds such as 3-methylcyclopentenone, (methyl) isobutyl ketones or 2-phenylpropionaldehyde, sec-butylbenzene, tert-butylbenzene, methylbenzenes, e.g. dimethylbenzene, or acetophenone (AP).

The process of the invention can be carried out in at least two different variants, but all of these comprise at least one distillation step and at least one phase separation step.

In a first embodiment of the process of the invention, the mixture is fractionated in at least one fractional distillation step, preferably in only a single distillation step, in such a way that a phenol-containing fraction containing less than 300 ppm of hydroxyacetone, preferably less than 100 ppm and very particularly preferably less than 10 ppm of hydroxyacetone, and a further fraction comprising at least hydroxyacetone, cumene and water are obtained and the latter fraction is separated into an organic phase and an aqueous phase in a phase separation step.

In this embodiment of the process of the invention, the mixture from which phenol is to be separated is first fed into a distillation apparatus, preferably a distillation column. The distillation column has to be configured so that it is possible to fractionate the mixture to give at least one phenol-containing fraction and at least one further fraction comprising at least cumene, water and hydroxyacetone. The mixture is preferably fed into the column at a side inlet, preferably in a position at which the column has a separation potential of from 25 to 85%, particularly preferably from 40 to 60%. The column is operated so that a phenol-containing fraction can be taken off in liquid form at the bottom of the column. It can be advantageous to feed part of this fraction back into the column. The phenol-containing fraction which is separated off at the bottom of the column and has a hydroxyacetone concentration of less than 300 ppm is preferably passed as crude phenol for further work-up.

The temperature at the bottom of column is preferably from 140 to 200° C., particularly preferably from 170 to 190° C. The temperature at the top of the column is preferably from 60 to 160° C., particularly preferably from 65 to 100° C. The temperature at the top of the column is always selected so that the temperature at the top is lower than the temperature at the bottom. The pressure in the column can be from 0.1 to 4 bar. The distillation column is preferably under atmospheric pressure.

The fraction taken off at the top of the column, preferably in vapor form, comprises at least water, cumene and hydroxyacetone. If AMS is present in the original mixture, AMS is also present in the top fraction. The top fraction preferably comprises at least from 95% to 100%, preferably from 98% to 99.9%, of the cumene present in the mixture, from 95% to 100%, preferably from 98% to 99.9%, of the hydroxyacetone present in the mixture and from 97% to 99.9% of the water present in the mixture.

Part of the fraction taken off at the top of the column can be fed back into the column in liquid form as runback. Preference is given to transferring at least part of the fraction taken off at the top of the distillation column to a phase separation apparatus, e.g. a decanter, coalescer, phase separation vessel or extractor, in which the fraction can be separated into an aqueous phase and an organic phase. It may be advantageous to return at least part of the organic phase of this fraction, at least part of the aqueous phase of this fraction or a mixture of organic and aqueous phase to the column as runback. The temperature at which phase separation is carried out is preferably from 20 to 100° C. at atmospheric pressure.

Very particular preference is given to returning at least part of the aqueous phase and part of the organic phase of the top fraction separated in the phase separation apparatus separately to the distillation column.

It may be advantageous to feed at least part of the aqueous phase back into the column in vapor or liquid form, preferably vapor form, at a point below the feed point.

The reflux ratio based on the amount of water taken off and the amount of water returned is preferably from 0.2 to 3, very particularly preferably from 0.4 to 2. The reflux ratio based on the amount of organic phase taken off and the amount of organic phase returned is preferably from 0.1 to 10, very particularly preferably from 0.5 to 5. The remainder of the organic part of the top fraction obtained from the phase separation apparatus is passed to further work-up. This organic part of the top fraction comprises at least cumene. The amount of hydroxyacetone in this organic part of the top fraction is from 0.01 to 10%, preferably from 0.1 to 2%, of the hydroxyacetone originally present in the top fraction.

The remainder of the aqueous part of the top fraction which is not recirculated to the distillation column can be passed to disposal or work-up. This aqueous part comprises the remaining hydroxyacetone from the top fraction which is not present in the organic part of the top fraction.

The advantage of the mode of operation according to the invention is that the hydroxyacetone present in the top fraction is concentrated in the water of this fraction. The predominant proportion (factor of 20–30) of the hydroxyacetone goes into the aqueous phase in the phase separation apparatus and can thus be discharged from the process in a simple manner with the aqueous part of the top fraction and does not have to be separated off from an organic phase as in the prior art (U.S. Pat. Nos. 4,251,325, 3,322,651 or U.S. Pat. No. 5,064,507; all incorporated herein by reference).

In a second embodiment of the process of the invention, the mixture is separated into an organic phase and an aqueous phase in at least one phase separation step and the organic phase obtained is fractionated in a fractional distillation step to give a phenol-containing fraction in which less than 300 ppm of hydroxyacetone are present.

In this embodiment of the process of the invention, the mixture from which phenol is to be separated is transferred to at least one phase separation apparatus, e.g. a decanter, coalescer, phase separation vessel or extractor, in which the mixture can be separated into an aqueous phase and an organic phase. The temperature at which the phase separation is carried out is preferably from 20 to 100° C. at atmospheric pressure.

The aqueous phase of the mixture can be passed to disposal or work-up, e.g. a phenol removal from wastewater and a water treatment plant, as are known in the art. A large part of the hydroxyacetone from the mixture is present in this aqueous phase.

The organic phase of the mixture obtained from the phase separation apparatus comprises at least cumene and phenol. The amount of hydroxyacetone in this organic phase of the mixture is from 10 to 60%, preferably from 30 to 40%, of the hydroxyacetone originally present in the mixture.

This organic phase of the mixture is then fed to a distillation apparatus, preferably a distillation column. The distillation column has to be configured so that it is possible to fractionate the mixture so as to give at least one fraction comprising phenol and at least one further fraction comprising at least cumene. The mixture is preferably fed into the column via a side inlet, preferably in a position at which the column has a separation potential of from 25 to 85%, particularly preferably from 40 to 60%. The column is operated so that a phenol-containing fraction can be taken off in liquid form at the bottom of the column. The phenol-containing fraction separated off at the bottom of the column, in which hydroxyacetone is present in a concentration of less than 300 ppm, is preferably passed as crude phenol for further work-up.

The temperature at the bottom of the column is preferably from 140 to 200° C., particularly preferably from 170 to 190° C. The temperature at the top of the column is preferably from 60 to 160° C., particularly preferably from 80 to 100° C. The temperature at the top of the column is always selected so that it is lower than the temperature at the bottom. The pressure in the column can be from 0.1 to 4 bar. The distillation column is preferably under atmospheric pressure.

The fraction taken off at the top of the column, preferably in vapor form, comprises at least cumene and hydroxyacetone. If AMS is present in the original mixture, AMS is also present in the top fraction. The top fraction preferably comprises from 95% to 100%, preferably from 98% to 99.9%, of the cumene present in the original mixture.

Part of the fraction taken off at the top of the column can be fed back into the column in liquid form as runback.

The advantage of the mode of operation according to the invention is that the hydroxyacetone is concentrated in the water. A predominant part of the hydroxyacetone goes into the aqueous phase in the phase separation apparatus and can thus be discharged from the process in a simple manner. Further treatment of the top fraction in this embodiment of the process of the invention in a phase separation apparatus also enables, as in the first embodiment of the process of the invention, the hydroxyacetone from the top fraction to be discharged via an aqueous phase separated off from the top product by phase separation.

In both embodiments of the process of the invention, very particular preference is given to obtaining a phenol-containing fraction which preferably comprises from 95 to 99% by weight of phenol and has a hydroxyacetone content of less than 300 ppm, preferably less than 100 ppm and very particularly preferably less than 10 ppm.

In both embodiments of the process of the invention, it can be advantageous to take off a further fraction comprising at least one organic and/or inorganic acid from the distillation apparatus in the distillation step via a side offtake. Such a fraction is preferably taken off from a side offtake located below the feed point for the mixture and above the bottom of the column. In this way, the proportion of by-products in the fraction can be reduced further.

In both embodiments of the process of the invention, it can be advantageous for further amounts of compounds which are already present in the mixture to be treated, to be added to this mixture. Particular preference is given to adding the compounds cumene and/or water or mixtures comprising cumene and/or water to the mixture to be treated. The addition can be carried out before or during the distillation step and/or before or during the phase separation step.

In the first embodiment of the process of the invention, it can be particularly advantageous to add such an amount of cumene and/or water to the mixture prior to the distillation that the water content of the mixture is from 1 to 14% by weight and the cumene content is from 1 to 50% by weight.

In the second embodiment, it can be advantageous to add water to the mixture before or during the phase separation step. It can likewise be advantageous to add cumene to the organic phase of the mixture prior to the distillation step. In the second embodiment, the cumene content of the organic part of the mixture before it is fed to the distillation step is preferably from 5 to 50% by weight.

In both embodiments of the process of the invention, the phenol obtained from the feed mixture not only contains less than 300 ppm of hydroxyacetone but is also depleted in impurities such as phenylbutenes, methylbenzofuran (MBF), mesityl oxide (MO), n-propylbenzene, isopropylphenol, carbonyl compounds such as 3-methylcyclopentenone, (methyl) isobutyl ketones or 2-phenylpropionaldehyde, sec-butylbenzene, tert-butylbenzene or methylbenzenes, e.g. dimethylbenzene. These impurities are separated from the mixture together with α-methylstyrene (AMS), cumene and water via the top of the distillation column or in the initial phase separation.

The fractions obtained according to the invention can be worked up further by methods known in the art.

The process of the invention for separating phenol from a mixture comprising at least hydroxyacetone, cumene, water and phenol is preferably carried out in an apparatus according to the invention.

This apparatus of the invention comprises at least one distillation column which is dimensioned so that an at least cumene- and/or α-methylstyrene-containing fraction can be taken off at the top of the column and a phenol-containing fraction having a hydroxyacetone content of less than 300 ppm, preferably less than 100 ppm and very particularly preferably less than 10 ppm, can be taken off at the bottom of the column and at least one phase separation apparatus for separating organic phases from aqueous phases.

The distillation column particularly preferably has at least from 20 to 160, particularly preferably from 40 to 80, theoretical plates. In a particularly preferred embodiment of the apparatus of the invention, it has a side off-take at which a fraction comprising at least one organic acid can be taken off located between the feed point for the mixture and the bottom of the column. The organic acid present in the fraction can be, for example, acetic acid, oxalic acid, formic acid or butyric acid or a mixture comprising at least one of these acids.

As phase separation apparatus, the apparatus of the invention preferably has at least one decanter.

Phenol is obtainable by the process of the invention. This phenol has a hydroxyacetone content of less than 300 ppm, particularly preferably less than 100 ppm and very particularly preferably less than 10 ppm. A cumene- and/or AMS-containing mixture having a reduced hydroxyacetone content can likewise be obtained by means of the process of the invention.

Figure 2:
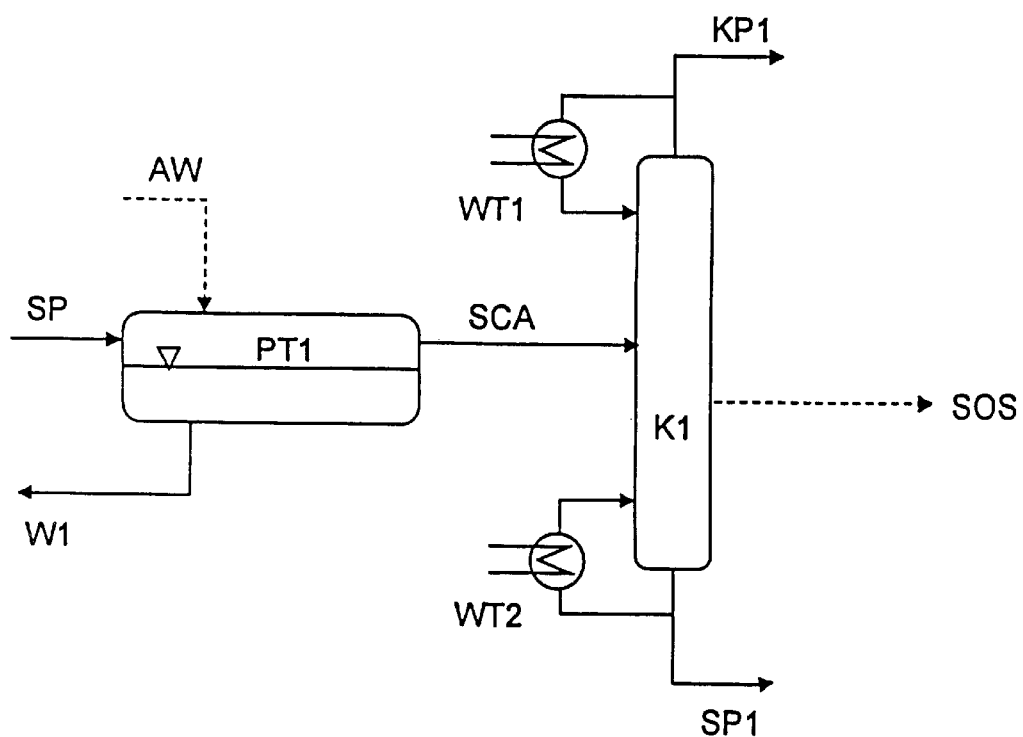

The process of the invention and the apparatus of the invention are shown by way of example in FIGS. 1 and 2 without the process or the apparatus being restricted to these embodiments.

FIG. 1 schematically shows an embodiment of the apparatus of the invention. The apparatus of the invention comprises a distillation column K1' which has a side inlet through which the mixture SP' can be fed in for the purpose of separating off the phenol. At the top and at the bottom of the column, the top product KP' and the bottom product SP1', respectively, can be taken off. The distillation column of the apparatus of the invention has, at the bottom of the column, a heat exchanger WT2' by means of which the appropriate heat energy can be introduced into the column.

From the top of the column, the top product KP' comprising at least cumene, hydroxyacetone and water is passed through a heat exchanger WT3' in which the top product is condensed, and the top product is transferred from there to a phase separation apparatus PT1'. Part of the organic phase formed in this phase separation apparatus can be returned to the distillation column via RO'. The remaining part of the organic phase, which comprises at least cumene, can be passed to further work-up via CA'. Part of the aqueous phase can likewise be returned in liquid form to the distillation column K1' via RW1'. A further part of the aqueous phase can be conveyed to the distillation column K1' in liquid or vapor form via RW2'. The remaining part of the aqueous phase, which comprises hydroxyacetone, can be passed via W1' to utilization or work-up. The distillation column K1' may optionally have one or more side offtakes SOS' via which fractions comprising at least one organic acid can be discharged from the column.

FIG. 2 schematically shows a further embodiment of the process of the invention. A mixture to be treated SP is fed into a phase separation apparatus PT1. The organic phase of the mixture, which comprises at least cumene and phenol, can be fed into a distillation column K1 at the side via SCA. The aqueous phase of the mixture, which comprises hydroxyacetone, can be passed via W1 to utilization or work-up. If necessary or desired, an aqueous phase or water can be introduced into the phase separation vessel via AW.

The organic phase of the mixture which is fed into the column K1 at the side via SCA is fractionated in the column to give a fraction which comprises at least cumene and is taken off at the top of the column as KP1 and a fraction which comprises at least phenol and can be taken off at the bottom of the column as SP1. The distillation column of the apparatus of the invention has runback systems at the top and at the bottom of the column by means of which some or all of the top product or bottom product can be returned to the column. The heat exchangers WT1 and WT2 are installed in these runback systems and make it possible to introduce or remove heat energy into/from the bottom or top product returned to the column. The distillation column K1 can optionally be provided with one or more side offtakes SOS via which fractions comprising at least one organic acid can be discharged from the column.

German patent application DE 100 60552.2 is hereby incorporated in its entirety by reference.

EXAMPLE 1

A mixture containing, 73 parts of phenol, 20 parts of cumene, 3 parts of AMS, 1 part of acetophenone, 0.2 part of hydroxyacetone and 2 parts of water, together with other materials, was fed at the side, at the height of the 40th theoretical plate, into a distillation column having 80 theoretical plates as shown in FIG. 1.

The temperature in the column was set so that the temperature at the top was 95° C. and the temperature at the bottom was 182° C. The pressure in the distillation column corresponded to atmospheric pressure. The fraction taken off at the top of the distillation column had a water content of 8% by weight, a cumene content of 79% by weight, a hydroxyacetone content of 0.8% by weight and an AMS content of 12% by weight. This fraction was transferred to a decanter. In this decanter, an aqueous phase comprising the major part of the hydroxyacetone present in the fraction was separated off from the fraction. Part of the aqueous phase was discarded. The remainder of the aqueous phase was returned to the distillation column.

The organic phase separated from the aqueous phase in the separation vessel had a hydroxyacetone content of less than 400 ppm. Part of this organic phase was returned to the distillation column. The remaining part of the organic phase was fed to a cumene column for the purpose of further work-up.

The fraction taken off from the bottom of the first distillation column comprised, inter alia, 98.5% by weight of phenol and 1.4% by weight of acetophenone and only 13 ppm of hydroxyacetone. This fraction was fed into a crude phenol column for the purpose of further work-up.

In this application, where number ranges are provided, all values between stated ranges are specifically included as if explicitly written out, as are subranges. The term "less than" a certain value includes all numbers below that value as if specifically written out.

What is claimed is:

1. A process for separating phenol from a mixture comprising at least hydroxyacetone, cumene, water and phenol, said process comprising
    feeding the mixture into a distillation apparatus,
    fractionally distilling the mixture to provide a phenol-containing fraction and a further fraction comprising at least hydroxyacetone, cumene and water,
    separating the further fraction into an aqueous phase and an organic phase, and
    returning at least a part of the aqueous phase to the distillation apparatus,
    wherein the phenol-containing fraction comprises less than 300 ppm of hydroxyacetone.

2. The process as claimed in claim 1, wherein the phenol-containing fraction comprises less than 30 ppm of hydroxyacetone.

3. The process as claimed in claim 1, wherein the mixture further comprises α-methyl-styrene.

4. The process as claimed in claim 1, wherein the mixture is a part of a cleavage product mixture obtained in an acid-catalyzed cleavage of cumene hydroperoxide.

5. The process as claimed in claim 1, wherein the mixture has a phenol concentration of from 20 to 90% by weight.

6. The process as claimed in claim 1, wherein the mixture has a hydroxyacetone concentration of from 300 ppm to 5% by weight.

7. A process for separating phenol from a mixture resulting from the cleavage of cumene hydroperoxide obtained after separating crude acetone from the cleavage product, wherein the mixture comprises at least hydroxyacetone, cumene, water and phenol, said process comprising separating the mixture into an aqueous and an organic phase, and fractionally distilling the organic phase to provide a phenol-containing fraction, wherein the phenol-containing fraction comprises less than 300 ppm of hydroxyacetone.

8. The process as claimed in claim 7, wherein the phenol-containing fraction comprises less than 30 ppm of hydroxyacetone.

9. The process as claimed in claim 7, wherein the organic phase comprises from 30 to 40% of the hydroxyacetone present in the mixture.

10. The process as claimed in claim 7, wherein the mixture further comprises α-methyl-styrene.

11. The process as claimed in claim 7, wherein said mixture is a part of a cleavage product mixture obtained in the acid-catalyzed cleavage of cumene hydroperoxide.

12. The process as claimed in claim 7, wherein the mixture has a phenol concentration of from 20 to 90% by weight.

13. The process as claimed in claim 7, wherein the mixture has a hydroxyacetone concentration of from 300 ppm to 5% by weight.

\* \* \* \* \*